(12) United States Patent
Maeng

(10) Patent No.: US 8,719,202 B1
(45) Date of Patent: May 6, 2014

(54) METHODS, DEVICES, AND MEDIUMS ASSOCIATED WITH MONITORING AND MANAGING EXERCISE FITNESS

(75) Inventor: Joon Maeng, Newcastle, WA (US)

(73) Assignee: Intellectual Ventures Fund 79 LLC, Las Vegas, NV (US)

( * ) Notice: Subject to any disclaimer, the term of this patent is extended or adjusted under 35 U.S.C. 154(b) by 269 days.

(21) Appl. No.: 13/302,540

(22) Filed: Nov. 22, 2011

(51) Int. Cl.
 *G06N 5/00* (2006.01)
 *A63B 15/02* (2006.01)
 *G06N 99/00* (2010.01)

(52) U.S. Cl.
 CPC .................................. *G06N 99/005* (2013.01)
 USPC ................................................ 706/45; 482/1

(58) Field of Classification Search
 None
 See application file for complete search history.

(56) References Cited

U.S. PATENT DOCUMENTS

| | | | |
|---|---|---|---|
| 8,083,643 B2 * | 12/2011 | Ng et al. | 482/1 |
| 2007/0011027 A1 * | 1/2007 | Melendez | 705/2 |
| 2007/0265138 A1 * | 11/2007 | Ashby | 482/8 |
| 2011/0082010 A1 * | 4/2011 | Dyer et al. | 482/9 |

OTHER PUBLICATIONS

Bionic Energy, LLC.; "About Bionic Energy"; 2010; 2 pages; http://www.bionicenergy.org/about.php (website accessed Dec. 28, 2011).

* cited by examiner

*Primary Examiner* — Alan Chen
(74) *Attorney, Agent, or Firm* — Stolowitz Ford Cowger LLP

(57) ABSTRACT

A method, device, or medium associated with monitoring and/or managing exercise fitness may include receiving substantially real-time vital data associated with a particular user and retrieving historic fitness data associated with the particular user. The historic fitness data may be updated with the real-time vital data, and the updated historic fitness data may be compared with a pre-existing fitness standard. A personalized fitness plan for re-aligning the updated historic fitness data with the pre-existing fitness standard may be generated based, at least in part, on a result of the comparing.

40 Claims, 6 Drawing Sheets

METHODS, DEVICES, AND MEDIUMS ASSOCIATED WITH MONITORING AND MANAGING EXERCISE FITNESS

BACKGROUND

Health clubs may have many types of known exercise equipment, such as treadmills, stationary bikes, rowing machines, stair climbers, and weight machines. The known types of exercise equipment may include options to select different modes of exercise or different levels of difficulty, and may provide a particular user with information, such as the duration of exercise. Other users of the known types of exercise equipment also may select different modes of exercise or different levels of difficulty and may obtain substantially similar information as the particular user, such as the duration of exercise.

The particular user may manage their fitness plan as part of their exercise regime by recording their exercise. Nevertheless, the known fitness equipment requires the particular user to manually enter their exercise plans and daily records, such as on a paper, in a notebook, or in a computer in order to monitor their progress.

DETAILED DESCRIPTION

Figure 1:
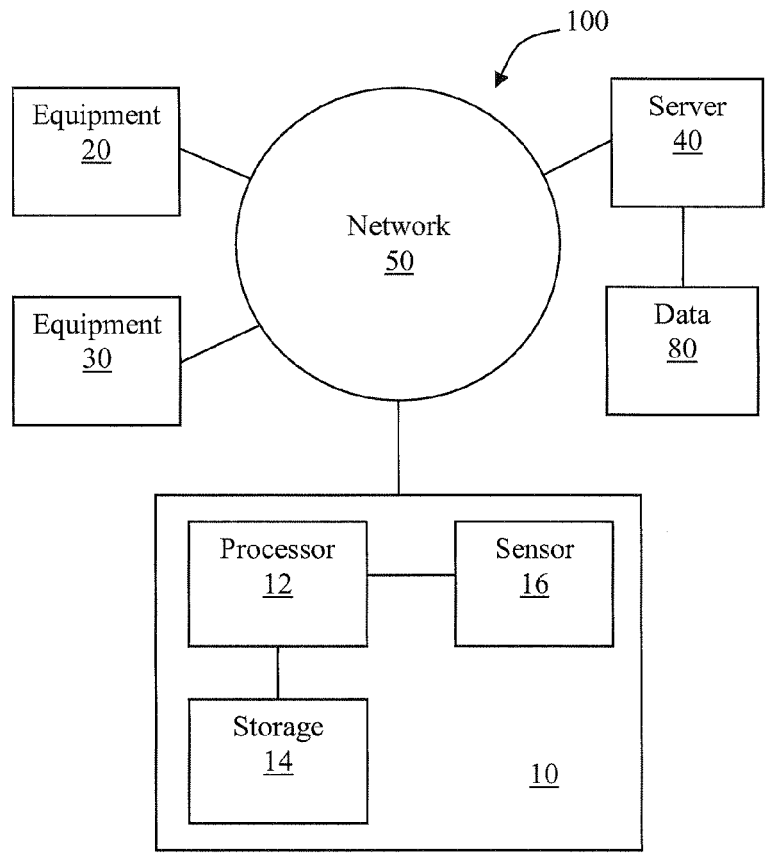
FIG. 1 depicts a block diagram of an example of a network associated with monitoring and/or managing exercise fitness.

FIG. 1 depicts a block diagram 100 of an example of a network 50 associated with monitoring and/or managing exercise fitness. A plurality of pieces of exercise equipment, including equipment 20 and equipment 30, may be operatively coupled to network 50. Equipment 20 and/or equipment 30 may be associated with one or more users.

Network 50 may comprise a public network or a private network established for personal use, business use, governmental use, or any combination thereof. For example, network 50 may comprise a cable network, a satellite network, a cellular network, a telephone network, a broadband network, a voice over Internet Protocol (VoIP) network, or any combination thereof. Furthermore, network 50 may comprise a wired network, a wireless network, a local area network, a wide area network, the Internet, a virtual network, or any combination thereof.

Network 50 may be operatively coupled to a device 10. Device 10 may be associated with a particular user. In one example, device 10 may be communicatively coupled to, may be integrated with, or may comprise a type of exercise equipment, such as a treadmill, a stationary bike, a rowing machine, a stair climber, a weight machine, other types of exercise equipment, or any combination thereof. Furthermore, device 10 may comprise a central processor, a mobile telephone, a smart-phone, a tablet, a personal computer, a laptop, a personal digital assistant (PDA), or any combination thereof.

Device 10 may comprise a processing device 12, one or more storage devices, such as a storage device 14, and one or more sensors 16 (hereafter referred to as sensors 16). Storage device 14 may be configured to store information associated with a piece of equipment, such as equipment 20 and/or equipment 30. The stored information may comprise subscription information, a user identification, a group identification, user vital data, community vital data and/or statistics, exercise plans, information associated with usage of exercise equipment, or any combination thereof.

Storage device 14 may be configured to store instructions associated with one or more processes, programs, and/or operations associated with monitoring and/or managing exercise fitness. Processing device 12 may be configured to execute the stored instructions. Processing device 12 may access storage device 14 to run, store, and/or archive one or more programs. Storage device 14 may comprise random access memory (RAM), read-only memory (ROM), and/or other types of storage or memory devices.

Processing device 12 may be configured to identify the particular user and/or to receive substantially real-time vital data associated with the particular user. In one example, processing device 12 may be configured to retrieve historic fitness data associated with the particular user, and to update the historic fitness data with the real-time vital data. Additionally, processing device 12 may be configured to compare the updated historic fitness data with a pre-existing fitness standard, and to generate a personalized fitness plan for re-aligning the updated historic fitness data with the pre-existing fitness standard based, at least in part, on a result of the comparing.

Device 10 may be configured to generate, access, submit, track, process, compare, retrieve, display, and/or present information, such as: a personalized exercise plan, a history of fitness activities, a fitness standard, a fitness recommendation, a healthcare concern, other information, or any combination thereof. The information may be associated with the particular user and/or with one or more other users. In one example, the information may be processed by a server 40 operatively coupled to network 50, and/or operatively coupled to device 10 via network 50.

Server 40 may be configured to perform some or all of the operations described above with respect to device 10 and/or processing device 12. A database 80 associated with server 40 may be configured to store information, such as subscription information, a user identification, a group identification, user vital data, community vital data and/or statistics, exercise plans, information associated with usage of exercise equipment, or any combination thereof.

Device 10 may be configured to provide access to one or more web portals from a piece of exercise equipment, such as equipment 20 and/or equipment 30. The particular user may access their associated information remotely, such as via a mobile device. The mobile device may comprise a mobile communication device and a software application, including instructions, that may be installed on the mobile communication device.

In one example, device 10 may comprise a web-portal operatively connected to a piece of exercise equipment, such as equipment 20 and/or equipment 30, through network 50.

Device 10 may be configured to transmit the personalized fitness plan from the web-portal to the mobile communication device and/or a personal computer.

Sensors 16 may comprise an identification sensor configured to identify and/or detect a particular user. Information associated with the particular user may be stored in storage device 14. The particular user may be identified by reading a Radio Frequency Identification (RFID) chip that comes into proximity with a piece of exercise equipment. In one example, the particular user may be identified by communicating with a mobile communication device associated with the particular user, using a short-range communication signal. In yet another example, the particular user may be identified based on a scanned bar code associated with the particular user.

Additionally, sensors 16 may comprise a sensor configured to monitor vital data and/or record an exercise fitness history associated with the particular user, such as a heart rate, a blood pressure, a respiratory rate, a caloric burn rate, other information associated with the particular user, or any combination thereof. The particular user may be identified by matching a biometric reading of the particular user against a database of users.

Device 10 may be configured to identify a deviation between the updated historic fitness data and the pre-existing fitness standard, and to generate an alert when the deviation indicates a health risk. The pre-existing fitness standard may be based, at least in part, on the historic fitness data of the particular user. In one example, the pre-existing fitness standard may be associated with a population of similarly-aged individuals as the particular user.

Figure 2:
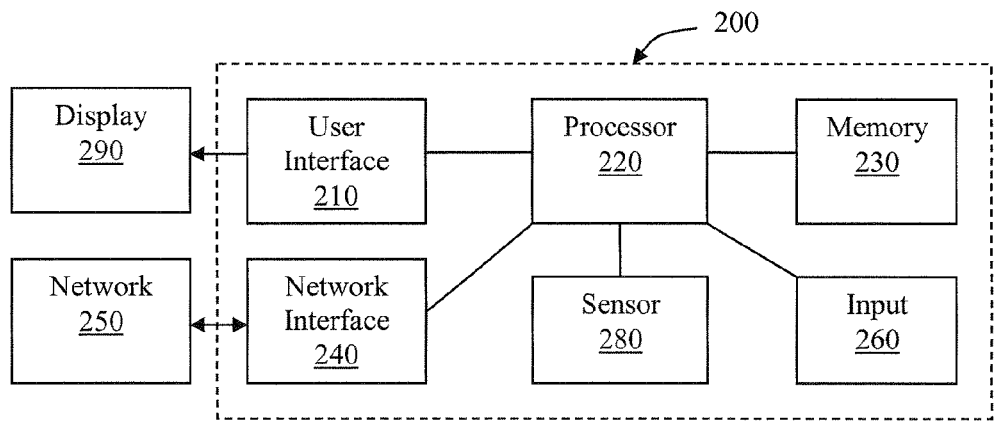
FIG. 2 depicts an example of an apparatus configured to monitor and/or provide management services associated with exercise fitness.

FIG. 2 depicts an example of an apparatus 200 configured to monitor and/or provide management services associated with exercise fitness. Apparatus 200 may comprise a processing device 220 operatively coupled to a memory device 230, one or more sensors 280 (hereafter referred to as sensors 280), a network interface 240, a user interface 210, and one or more input devices 260 (hereafter referred to as input devices 260).

Network interface 240 may comprise electronic circuits or programs configured to interface and/or communicate with a network 250, such as a wired network, a wireless network, or any combination thereof. Network interface 240 may be configured to provide one or more network connections to a local area network associated with a fitness center. Network interface 240 also may be configured to interface with a mobile device, such as a smart-phone, using a personal area network, such as Bluetooth or Zigbee. In one example, and substantially similar to network 50 as described with respect to FIG. 1, network 250 may operatively couple apparatus 200 to a plurality of pieces of exercise equipment, such as equipment 20 and/or equipment 30 (FIG. 1).

Sensors 280 may comprise an optical sensor, a radio frequency (RF) sensor, a magnetic sensor, an electromagnetic sensor, other types of sensors, or any combination thereof. Sensors 280 may be packaged as, and/or associated with, a camera, a magnetic card reader, a barcode reader, an RF identification (RFID) reader, an optical sensor, or any combination thereof.

Memory device 230 may be configured to store instructions associated with an application program. Processing device 220 may be configured to execute the stored instructions. Processing device 220 also may be configured to access memory device 230 to run, store, and/or archive one or more programs. Memory device 230 may comprise RAM, ROM, and/or other types of storage or memory devices.

Processing device 220 may be configured to manage and/or to monitor information associated with exercise fitness. Processing device 220 additionally may be configured to receive input and/or commands from user interface 210 and/or input devices 260. Input devices 260 may comprise activity sensors, vital sign sensors, or any combination thereof. Processing device 220 may be configured to receive, process, transfer, and/or present signals to display device 290 or a fitness server, such as server 40 (FIG. 1), or any combination thereof.

User interface 210 may be operatively coupled to a display 290. Display 290 may comprise a liquid crystal diode (LCD) display, a light emitting diode (LED) display, a computer, a television, a monitor, a smart-phone, a plasma screen, a projection screen, other types of display devices, or any combination thereof. User interface 210 may comprise one or more buttons to operate a piece of fitness equipment. In one example, display 290 and/or user interface 210 may provide for, or may be configured with, touch-screen controls.

User interface 210 and/or display 290 may be configured to display subscription information, user identification, group identification, user vital data, community vital data and/or statistics, exercise plans, information associated with usage of exercise equipment, or any combination thereof. In one example, a personalized fitness plan tailored to the particular user may comprise both an exercise program and a dietary program.

Apparatus 200 may be configured to identify a particular user and to receive substantially real-time vital data associated with the particular user. Input devices 260 and/or sensors 280 may comprise a bar code scanner, a camera, an identification card reader, a Radio Frequency Identification (RFID) reader, or any combination thereof, for identifying the particular user.

Additionally, apparatus 200 may be configured to retrieve historic fitness data associated with the particular user and to update the historic fitness data with the real-time vital data. In one example, the updated historic fitness data may be compared with a pre-existing fitness standard to generate a personalized fitness plan for re-aligning the updated historic fitness data with the pre-existing fitness standard based, at least in part, on a result of the comparing.

Vital data associated with the particular user may be received and/or measured while the particular user is operating a piece of exercise equipment. The vital data may comprise a heart rate, a blood pressure, a respiratory rate, a caloric burn rate, other information associated with the particular user, or any combination thereof. The pre-existing fitness standard may be based, at least in part, on vital data associated with a particular mode of exercise using the piece of exercise equipment. Additionally, the pre-existing fitness standard may be based, at least in part, on historic vital data associated with the particular user and/or other users.

Apparatus 200 may be configured to generate an alert when the real-time vital data indicates a deviation from the historic fitness data. The alert may comprise an audible and/or visual indication of a health concern to the particular user. In one example, the alert may be transmitted to a service provider, including, without limitation, a medical response team, a hospital, a physician, an insurance provider, a trainer, a fitness center, an emergency contact, or any combination thereof.

Figure 3:
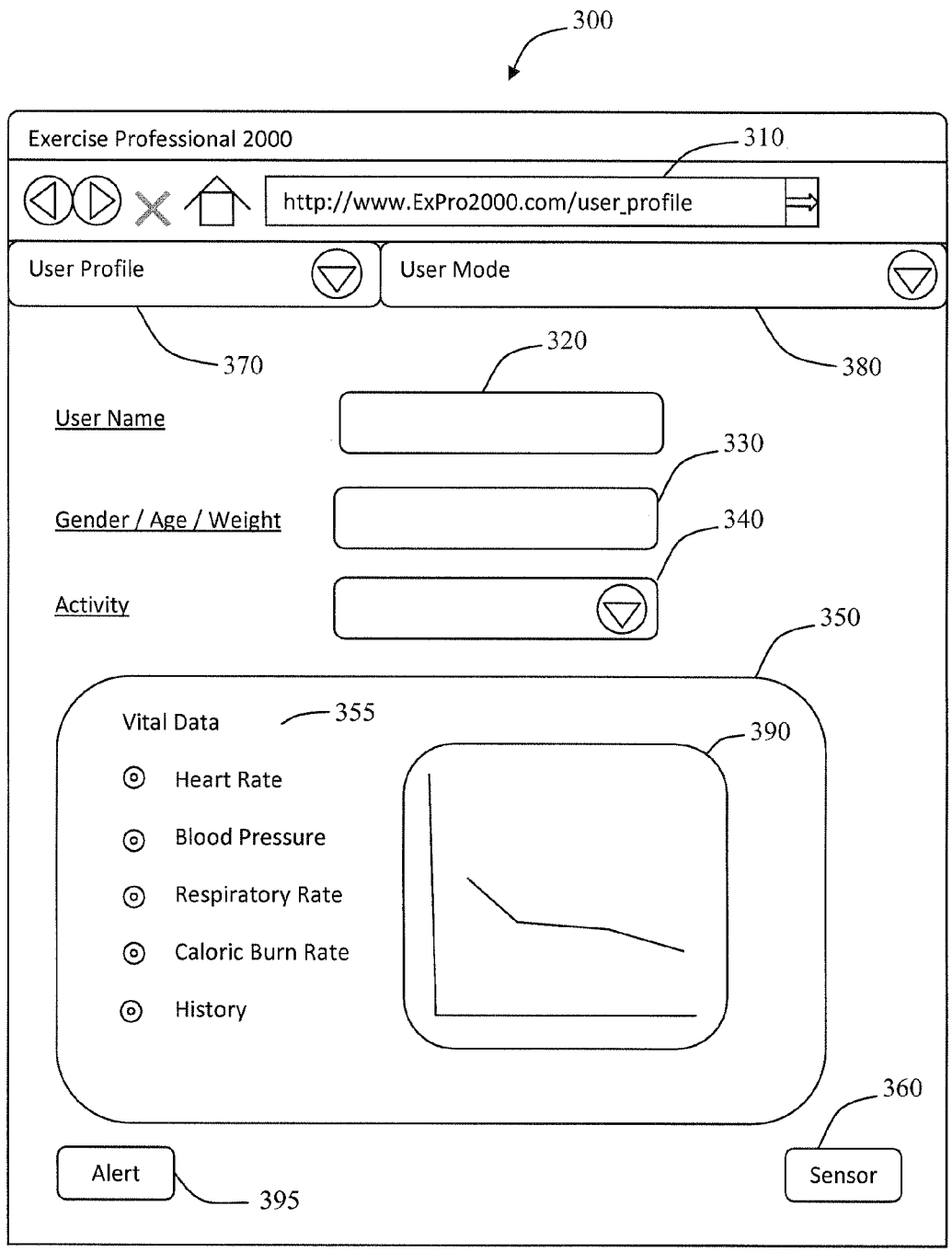
FIG. 3 depicts an example of a user interface configured to monitor and/or provide management services associated with exercise fitness.

FIG. 3 depicts an example of a user interface 300 configured to monitor and/or provide management services associated with exercise fitness. User interface 300 may be operatively coupled to, and/or may comprise, an input screen, a display device, a computer, a television, a monitor, a smart-phone, a plasma screen, a LCD screen, a projection screen, a voice activated system, a key entry system, a text entry system, or any combination thereof. User interface 300 may be associated with a server, a service provider, a browser, a central processor, a mobile telephone, a smart-phone, a tablet, a personal computer, a laptop, a personal digital assistant (PDA), or any combination thereof. In one example, user interface 300 may be operatively coupled to a piece of exercise equipment.

User interface 300 may be configured to communicate with a server over a network, and may be associated with one or more network addresses, such as network address 310. Information associated with network address 310 may be used to populate one or more fields of user interface 300. The information may be associated with a particular user's name 320 who has logged in to a network system, for example. User interface 300 may be configured to display different types of information or user options, such as a user profile 370. In addition to identifying the particular user or user name 320, user profile 370 may include personal information 330 associated with the user, such as gender, age, weight, or any combination thereof.

User interface 300 may be configured to provide the user with a selection of user modes 380. For example, user modes 380 may include options for selecting subscription information, a user identification, a group identification, user vital data, community vital data and/or statistics, exercise plans, information associated with usage of exercise equipment, or any combination thereof.

User modes 380 may include an option for the user to enter an exercise goal. For example, the user may select a goal of losing a particular amount of weight over a certain time period. Responsive to the exercise goal, user interface 300 may be configured to generate a personalized fitness plan comprising one or both of an exercise program and a dietary program. User interface 300 may be configured to monitor the user's progress in meeting the exercise goal and/or modify the personalized fitness plan accordingly.

Additionally, user interface 300 may be configured to monitor usage of one or more pieces of equipment, record user activity associated with the usage, including vital data 355 and/or vital statistics, present the user's fitness results on a display 350, or any combination thereof. Vital data 355 may include heart rate, blood pressure, respiratory rate, caloric burn rate, other information associated with the particular user, or any combination thereof. A history 390 of the user's vital data 355 may be charted and/or displayed as a function of time.

In one example, vital data 355 may be charted and/or compared with vital data associated with a plurality of users having a similar age, gender, and/or weight as the particular user. If vital data 355 is found to vary substantially from vital data associated with the plurality of similar users and/or with the history 390 of vital data associated with the particular user, user interface 300 may be configured to generate an alert 395. Alert 395 may indicate an imminent health risk and/or indicate that the particular user needs to reduce the level of physical exertion associated with an activity 340.

User interface 300 may include an option for selecting different types of activities, such as activity 340. The activity 340 may be associated with the same piece of exercise equipment, for example, by providing varying levels of difficulty and/or duration, and/or with multiple types of exercise equipment.

The particular user may be identified and/or authenticated when the particular user logs in to the system through user interface 300. One or more sensors 360 may be configured to identify the particular user and/or monitor vital data 355 associated with the particular user.

Figure 4:
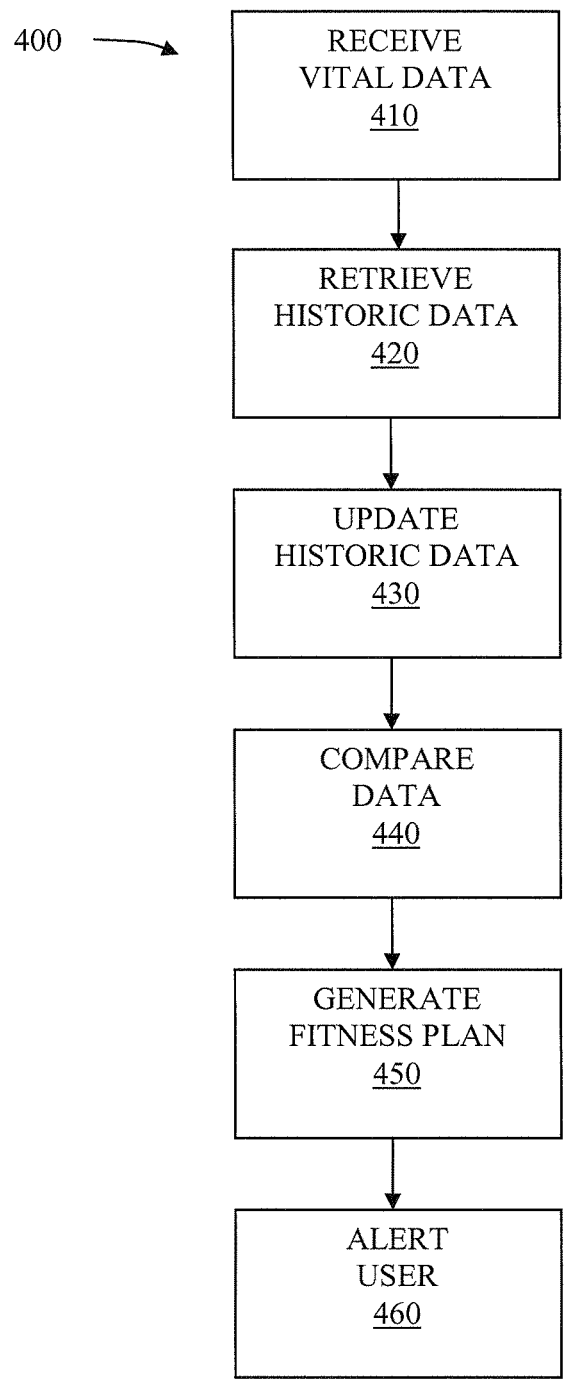
FIG. 4 depicts an example of a process for monitoring and/or providing management services associated with exercise fitness.

FIG. 4 depicts an example of a process 400 for monitoring and/or providing management services associated with exercise fitness. At operation 410, substantially real-time vital data associated with a particular user may be received. The real-time vital data may comprise a heart rate, a blood pressure, a respiratory rate, a caloric burn rate, other information associated with the particular user, or any combination thereof.

In one example, the identification of the particular user may be received from a piece of exercise equipment that is being operated by the particular user. The exercise equipment may be operatively coupled to a processing device through a local area network and/or through a wide area network.

At operation 420, historic fitness data associated with the particular user may be retrieved. The historic fitness data may be retrieved from a storage device, a memory device, a communication device, a processing device, a server, or any combination thereof. The historic fitness data may be associated with prior activities of the particular user. The prior activities may be associated with exercise using the same or similar pieces of exercise equipment, and/or with a plurality of different types of equipment. In one example, the vital data may be associated with operation of a piece of exercise equipment, and the historic fitness data may be associated with vital data received from a plurality of other exercise equipment that were operated by the particular user.

At operation 430, the historic fitness data may be updated with the real-time vital data. The historic fitness data may comprise separate data entries corresponding to different dates and/or activities. In one example, the historic fitness data may comprise a combined and/or weighted average of multiple activities to determine a normalized fitness level associated with the particular user.

At operation 440, the updated historic fitness data may be compared with a pre-existing fitness standard. The pre-existing fitness standard may be based, as least in part, on the historic fitness data prior to being updated with the real-time vital data. In one example, the updated historic fitness data may be compared with the pre-existing fitness standard to identify a deviation of the real-time vital data from the historic fitness data.

At operation 450, a personalized fitness plan for re-aligning the updated historic fitness data with the pre-existing fitness standard may be generated based, at least in part, on a result of the comparing.

At operation 460, an alert may be generated when the real-time vital data indicates a deviation from the historic fitness data. In one example, the alert may be generated in response to identifying the deviation of the real-time vital data from the historic fitness data.

The pre-existing fitness standard may be associated with a population of similarly-aged individuals as the particular user. The alert may be generated when the vital data is inconsistent with an expected input of the particular user, based on the population of similarly-aged individuals.

Figure 5:
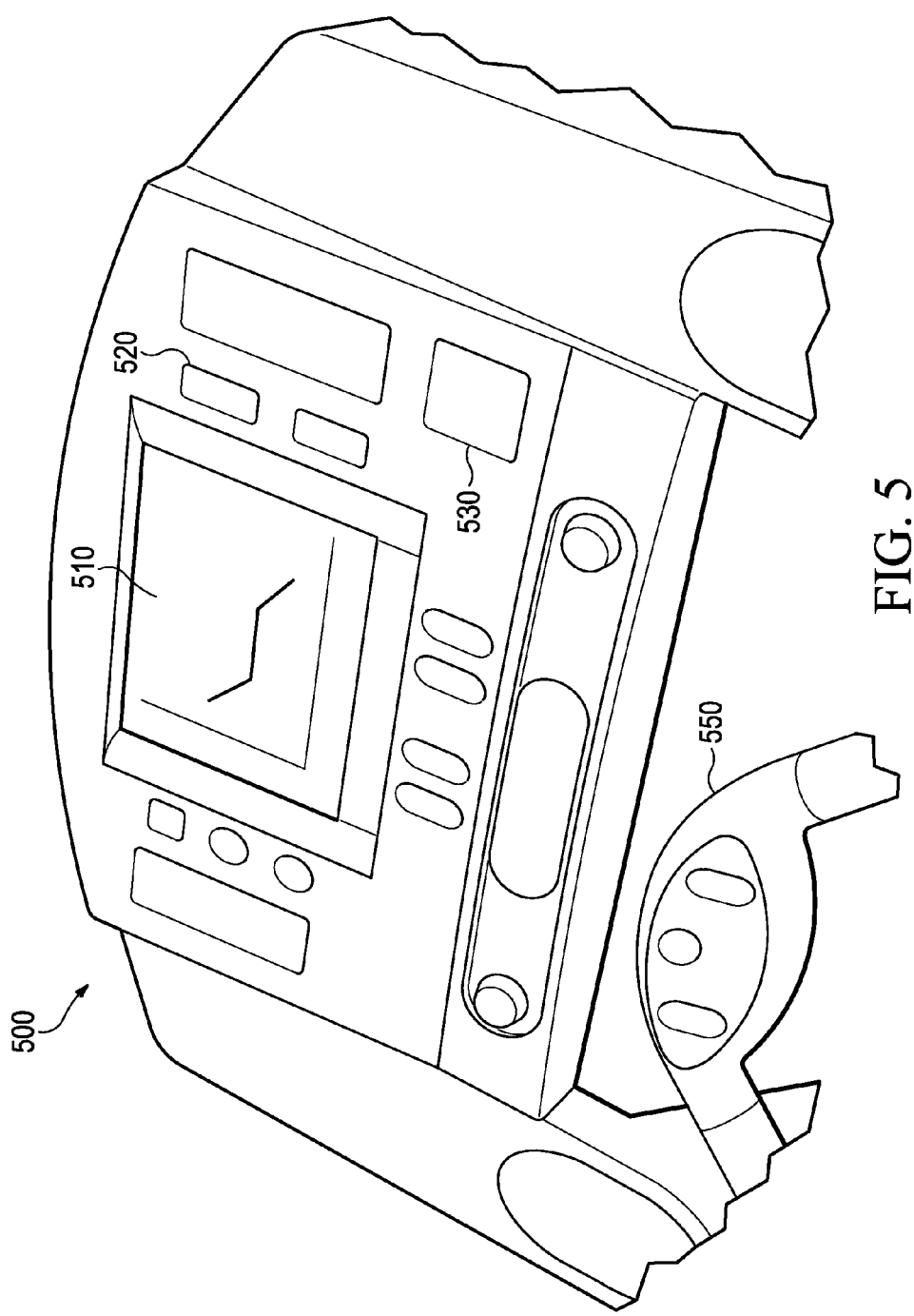
FIG. 5 depicts a piece of exercise equipment including a system for monitoring and/or managing exercise fitness.

FIG. 5 depicts a piece of exercise equipment 550 including a system 500 configured to monitor and/or manage exercise fitness. System 500 may comprise a display 510, one or more control buttons 520, and a sensor 530. In one example, the particular user may place an identification card, such as a health club membership card, over sensor 530. Sensor 530 may be configured to identify the particular user and to present a personal fitness program on display 510. The particular user may select a fitness program and begin exercising. System 500 may be configured to record the exercise and store the results in a server in a local area network. In one example, system 500 may sense and/or record vital data associated with the particular user during the exercise.

System 500 may be configured to display the exercise history, vital data, analytics, plans, guidelines, or any combination thereof, on exercise equipment 550 and/or on a mobile device, such as a smart-phone. System 500 may be configured to transfer the exercise history to a web portal and/or server for management of the particular user's exercise fitness data.

Additionally, system 500 may be configured to identify the particular user. For example, sensor 530 may comprise a barcode reader configured to read a barcode and/or magnetic strip included on an identification card. Sensor 530 may comprise a camera configured to capture membership information on the identification card. In some examples, sensor 530 may be configured to read an RFID associated with the particular user and/or to read user information displayed on a mobile communication device.

Figure 6:
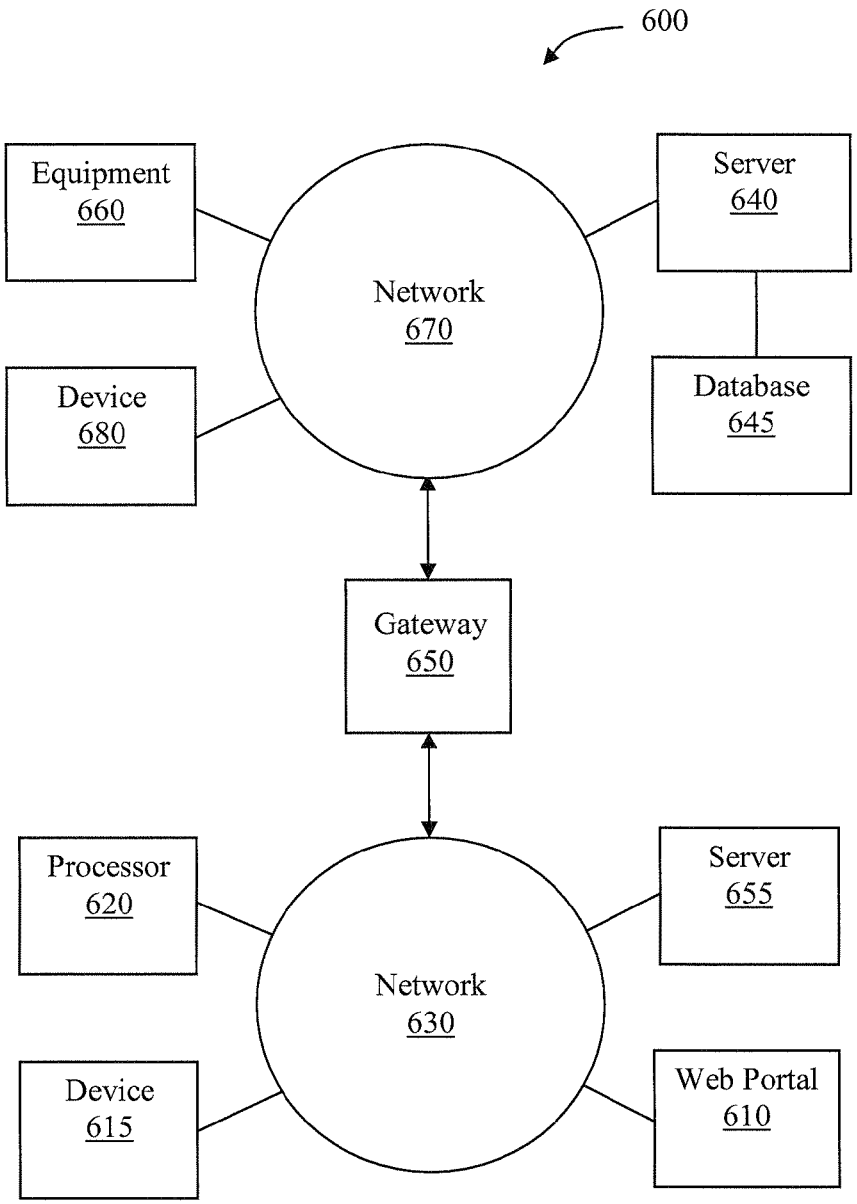
FIG. 6 depicts an example of a network system configured to monitor and/or provide management services associated with exercise fitness.

FIG. 6 depicts an example of a network system 600 configured to monitor and/or provide management services associated with exercise fitness. System 600 may comprise fitness equipment 660, one or more servers, such as first server 640 and/or a second server 655, a first network 670, a database 645, one or more user devices, such as device 615 and/or device 680, a second network 630, a processing device 620, a web portal 610, and a gateway 650.

First network 670 may comprise a wireless network, a wire-line network, a local area network, a public network, a private network, or any combination thereof. For example first network 670 may be associated with a business, a home, a fitness center, a health club, a work place, an apartment complex, a residence, a community center, a park, a school, or any combination thereof. Server 640 may be configured to receive data from, and/or transmit data to, fitness equipment 660, device 680, processing device 620, server 655, device 615, web portal 610, or any combination thereof. Data transmitted from and/or to server 640 may be stored in database 645.

Second network 630 may comprise a wide area network, a cellular network, a public network, a private network, the Internet, or any combination thereof. Gateway 650 may comprise a router, a server, a modem, or any combination thereof, and may be configured to operatively couple first network 670 to second network 630. Additionally, gateway 650 may be configured to provide protection for first network 670 from SPAM, viruses, malicious attacks, unauthorized access, or any combination thereof. Second network 630 may be configured to provide network connections for processing device 620, device 615, second server 655, web portal 610, or any combination thereof.

Fitness equipment 660 may be associated with network 670, for example, by being located at the associated business, home, fitness center, health club, work place, apartment complex, residence, community center, park, school, or any combination thereof. Fitness equipment 660 may be configured to transmit information to first server 640 and/or second server 655. In one example, first server 640 may be configured to manage user access rights and/or user information associated with a particular user.

Device 615 and/or device 680 may be configured to access the user information stored in database 645, via first server 640. Device 680 may be configured to communicate with first server 640 over first network 670. Device 615 may be configured to communicate with first server 640 via second network 630. In one example, device 615 and/or device 680 may comprise a wireless and/or mobile communication device, such as a smart-phone.

First server 640 and/or second server 655 may be configured to transfer user information to web portal 610. Web portal 610 may be configured to provide monitoring and/or management services associated with a particular user. The information and/or management services may be associated with exercise management, a dietary program, data on health conditions, vital data, fitness targets, fitness standards, other health and wellness related activities, or any combination thereof. In one example, web portal 610 may be managed by a service provider associated with first server 640 and/or second server 655. Web portal 610 may be configured to provide a device with access to the user information and/or management services. The device may be configured with a web browser and access rights.

Second server 655 may be associated with a service provider that manages fitness data for a plurality of distributed locations and/or fitness centers. In one example, device 615 may be configured to access user information associated with usage of fitness equipment 660 via second server 655 and/or web portal 610.

System 600 may be configured to receive substantially real-time vital data associated with a particular user. In one example, server 640 may be configured to receive the real-time vital data from fitness equipment 660. Additionally, system 600 may be configured to retrieve historic fitness data associated with the particular user and to update the historic fitness data with the real-time vital data. The historic fitness data may be stored in database 645. In one example, the vital data may comprise a heart rate, a blood pressure, a respiratory rate, a caloric burn rate, other user information associated with the particular user, or any combination thereof.

In one example, the vital data may be received from a personal digital assistant (PDA), and the PDA may be configured to transmit the vital data to a piece of fitness equipment, such as fitness equipment 660, and/or to a processing device, via a network, such as first network 670 and/or second network 630. The PDA may be configured to wirelessly transmit the vital data via a mobile communication network.

System 600 may be configured to compare the historic fitness data with a pre-existing fitness standard, and to generate a personalized fitness plan for re-aligning the historic fitness data with the pre-existing fitness standard based, at least in part, on a result of the comparing. In one example, the pre-existing fitness standard may be based, at least in part, on the historic fitness data of the particular user. Additionally, or in the alternative, the pre-existing fitness standard may be associated with a population of individuals sharing a similar health profile as the particular user.

System 600 may be configured to identify a deviation between the real-time vital data and the historic fitness data, and to generate an alert in response to identifying the deviation. In response to identifying a deviation between the updated historic fitness data and the pre-existing fitness standard, system 600 may be configured to generate an alert when the deviation from the pre-existing fitness standard exceeds a normalized threshold.

In one example, a user's vital data may be monitored and/or recorded in real-time by processing device 620 while the user is performing a first activity, such as jogging in the park. Processing device 620 may be configured to compare the user's vital data with historic fitness data associated with a second activity, such as using exercise equipment 660. In one example, the user's vital data may be transmitted by device 615 to a server, such as first server 640, which performs the comparison.

The historic fitness data may provide a fitness standard to determine a real-time health status of the user. For example, if the comparison of the vital data with the historic fitness data indicates a health risk, processing device 620 and or device 615 may alert the user to stop jogging. Vital data associated with the first activity also may be transmitted to a server to update the historic fitness data associated with the user. Accordingly, the historic fitness data may represent vital data accumulated during a plurality of different activities associated with the user and/or at different locations associated with one or more activities.

Figure 7:
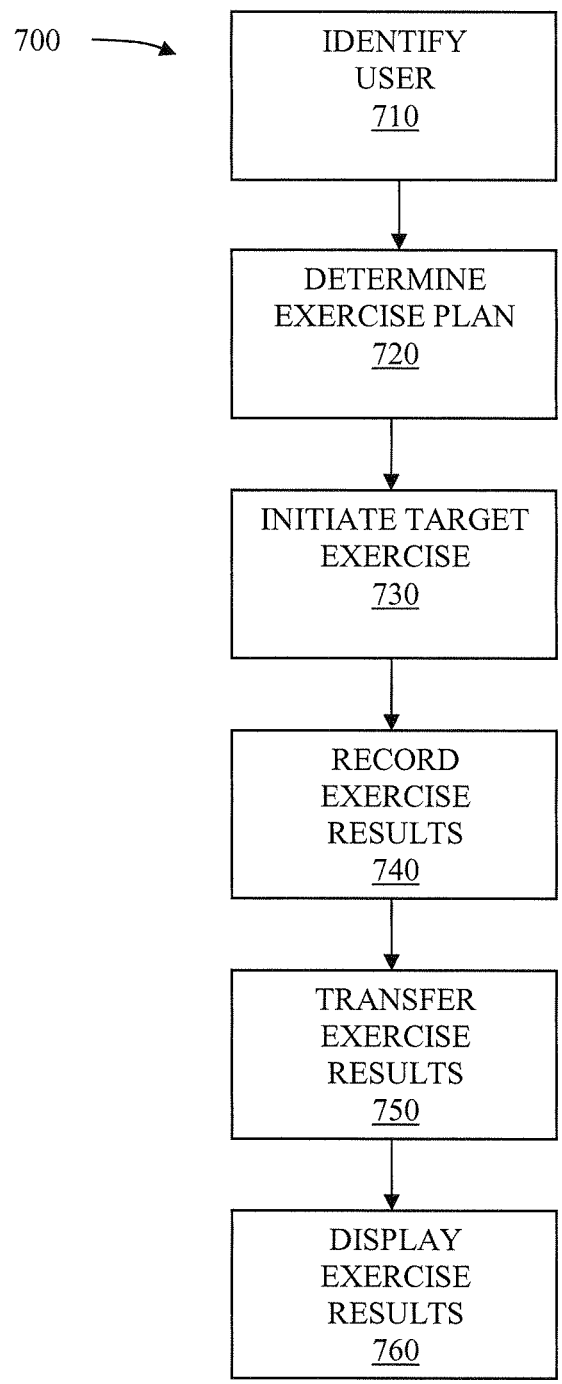
FIG. 7 depicts a further example of a process for monitoring and/or providing management services associated with exercise fitness.

FIG. 7 depicts a further example of a process 700 configured to monitor and/or provide management services associated with exercise fitness. At operation 710, a user may be identified. For example, a particular user may be identified according to information associated with an identification card, a biometric reading, a retinal scan, voice recognition, a fingerprint, a password, other forms of identification, or any combination thereof.

At operation 720, an exercise plan associated with the particular user may be determined. The exercise plan may correspond to a predetermined exercise plan and/or the exercise plan may be based, at least in part, on previous exercise activities associated with the particular user. The exercise plan may be retrieved from a database and presented on a display device, for example, in response to a server receiving the identification of the particular user.

At operation 730, a target exercise activity may be initiated, for example, on a piece of exercise equipment. The target exercise activity may comprise a particular mode of operation and/or level of difficulty associated with the exercise equipment. The target exercise activity may be identified by, and/or as part of, the exercise plan.

At operation 740, results associated with the target exercise activity may be monitored and/or recorded. The exercise results may be recorded during a time period and/or a duration of the target exercise activity. In one example, the exercise results may be determined based, at least in part, on a comparison between information associated with the particular user and information associated with a population of other users. The exercise results may indicate a general health of the particular user in relationship to the other users, and/or the progress of the particular user in relationship with a target exercise plan and/or goal.

At operation 750, the exercise results may be transferred to a device. In one example, the exercise results may be transferred from a piece of exercise equipment to a server, a processing device, a communication device, a PDA, or any combination thereof. Additionally, the exercise results may be transferred from a server to a piece of exercise equipment, a processing device, a communication device, a PDA, or any combination thereof.

At operation 760, the exercise results may be displayed on a display device. The display device may comprise an LCD display, an LED display, a computer, a television, a monitor, a smart-phone, a PDA, a plasma screen, a projection screen, other types of display devices, or any combination thereof.

The exemplary processes 400 and/or 700 depicted by FIG. 4 and FIG. 7, respectively, and the associated operations described therein, may be performed by one or more processing devices, such as processing device 12, processing device 220, system 500, processing device 620, first server 640, second server 655, and/or equipment 660 as depicted by FIGS. 1, 2, 5, and 6, respectively.

The system and apparatus described above may use dedicated processor systems, micro controllers, programmable logic devices, microprocessors, or any combination thereof, to perform some or all of the operations described herein. Some of the operations described above may be implemented in software and other operations may be implemented in hardware. One or more of the operations, processes, and/or methods described herein may be performed by an apparatus, a device, and/or a system substantially similar to those as described herein and with reference to the illustrated figures.

The processing device may execute instructions or "code" stored in memory. The memory may store data as well. The processing device may include, but may not be limited to, an analog processor, a digital processor, a microprocessor, a multi-core processor, a processor array, a network processor, or the like. The processing device may be part of an integrated control system or system manager, or may be provided as a portable electronic device that may be configured to interface with a networked system, locally and/or remotely, via a wireless transmission.

The processor memory may be integrated together with the processing device, for example RAM or FLASH memory disposed within an integrated circuit microprocessor or the like. In other examples, the memory may comprise an independent device, such as an external disk drive, a storage array, a portable FLASH key fob, or the like. The memory and processing device may be operatively coupled together, or in communication with each other, for example by an I/O port, a network connection, or the like, and the processing device may read a file stored on the memory. Associated memory may be "read only" by design (ROM) by virtue of permission settings, or not. Other examples of memory may include, but may not be limited to, WORM, EPROM, EEPROM, FLASH, or the like, which may be implemented in solid state semiconductor devices. Other memories may comprise moving parts, such as a known rotating disk drive. All such memories may be "machine-readable" and may be readable by a processing device.

Operating instructions or commands may be implemented or embodied in tangible forms of stored computer software (also known as "computer program" or "code"). Programs, or code, may be stored in a digital memory and may be read by the processing device. "Computer-readable storage medium" (or alternatively, "machine-readable storage medium") may include all of the foregoing types of memory, as well as new technologies of the future, as long as the memory may be capable of storing digital information in the nature of a computer program or other data, at least temporarily, and as long as the stored information may be "read" by an appropriate processing device. The term "computer-readable" may not be limited to the historical usage of "computer" to imply a complete mainframe, mini-computer, desktop or even laptop computer. Rather, "computer-readable" may comprise storage medium that may be readable by a processor, a processing device, or any computing system. Such media may be any available media that may be locally and/or remotely accessible by a computer or a processor, and may include volatile and non-volatile media, and removable and non-removable media, or any combination thereof.

A program stored in a computer-readable storage medium may comprise a computer program product. For example, a storage medium may be used as a convenient means to store or transport a computer program. For the sake of convenience, the operations may be described as various interconnected or coupled functional blocks or diagrams. However, there may be cases where these functional blocks or diagrams may be equivalently aggregated into a single logic device, program or operation with unclear boundaries.

Having described and illustrated the principles of various examples, it should be apparent that the examples may be modified in arrangement and detail without departing from such principles. We claim all modifications and variation coming within the spirit and scope of the following claims.

The invention claimed is:

1. A method comprising:
receiving, by a processing device, real-time vital data associated with a particular user;
retrieving, by the processing device, historic fitness data associated with the particular user;
updating, by the processing device, the historic fitness data with the real-time vital data;
receiving, by the processing device, vital data from a plurality of group members having a similar age as the particular user;
combining, by the processing device, the vital data from the plurality of group members into a pre-existing fitness standard;
comparing, by the processing device, the updated historic fitness data with the pre-existing fitness standard; and
generating, by the processing device, a personalized fitness plan for re-aligning the updated historic fitness data with the pre-existing fitness standard based, at least in part, on a result of the comparing.

2. The method of claim 1, wherein an identification of the particular user is received from a piece of exercise equipment that is being operated by the particular user.

3. The method of claim 2, wherein the exercise equipment is operatively coupled to the processing device through a local area network.

4. The method of claim 2, wherein the exercise equipment is operatively coupled to the processing device through a wide area network.

5. The method of claim 1, further comprising generating an alert, by the processing device, when the real-time vital data indicates a deviation from the historic fitness data.

6. The method of claim 1, wherein the pre-existing fitness standard is based, as least in part, on the historic fitness data prior to being updated with the real-time vital data, and wherein the updated historic fitness data is compared with the pre-existing fitness standard to identify a deviation of the real-time vital data from the historic fitness data.

7. The method of claim 6, further comprising generating an alert, by the processing device, in response to identifying the deviation.

8. The method of claim 1, wherein the real-time vital data is received from exercise equipment while being operated by the particular user and further comprising transmitting, by the processing device, the updated historic fitness data and the pre-existing fitness standard back to a display device on the exercise equipment.

9. The method of claim 8, further comprising generating an alert to a medical response service, by the processing device, when the real-time vital data is inconsistent with the pre-existing fitness standard.

10. The method of claim 1, wherein the real-time vital data is further associated with operation of exercise equipment, and wherein the historic fitness data comprises real-time vital data received from a plurality of other exercise equipment operated by the particular user.

11. A memory device having instructions stored thereon that, in response to execution by a processing device, cause the processing device to perform operations comprising:
receiving real-time vital data associated with a particular user while the particular user is exercising on fitness equipment;
retrieving historic fitness data associated with the particular user;
updating the historic fitness data with the real-time vital data;
comparing the historic fitness data with a pre-existing fitness standard, wherein the pre-existing fitness standard is derived at least in part from real-time fitness data received from a population of similarly-aged individuals as the particular user;
generating a personalized fitness plan for re-aligning the historic fitness data with the pre-existing fitness standard based, at least in part, on a result of the comparing;
generating an alert when the real-time vital data indicates a deviation from the pre-existing fitness standard; and
transmitting the alert to a medical service provider.

12. The memory device of claim 11, further comprising transmitting the historic fitness data and the pre-existing fitness standard to a display on the fitness equipment.

13. The memory device of claim 11, wherein the pre-existing fitness standard is associated with a population of individuals sharing a similar health profile as the particular user.

14. The memory device of claim 11, wherein the real-time vital data comprises a heart rate associated with the particular user.

15. The memory device of claim 11, wherein the operations further comprise:
identifying a deviation between the real-time vital data and the historic fitness data; and
generating the alert in response to identifying the deviation.

16. The memory device of claim 11, wherein the operations further comprise
generating the alert when the deviation from the pre-existing fitness standard exceeds a normalized threshold.

17. The memory device of claim 11, wherein the real-time vital data is received from the fitness equipment, and wherein the pre-existing fitness standard is based, at least in part, on a particular mode of exercise associated with the fitness equipment.

18. The memory device of claim 11, wherein the real-time vital data is received from a personal digital assistant (PDA).

19. The memory device of claim 18, wherein the PDA transmits the real-time vital data to the fitness equipment operatively connected to the processing device via a network.

20. The memory device of claim 18, wherein the PDA wirelessly transmits the real-time vital data to the processing device via a mobile communication network.

21. An apparatus, comprising:
a memory device configured to store instructions; and
a processing device that, in response to executing the instructions stored in the memory device, is configured to:
identify a particular user;
receive real-time vital data generated by exercise equipment operated by the particular user;
retrieve historic fitness data associated with the particular user;
update the historic fitness data with the real-time vital data;
retrieve a pre-existing fitness standard comprising, at least in part, vital data for a plurality of other individuals;
compare the updated historic fitness data with the pre-existing fitness standard;
generate a personalized fitness plan for re-aligning the updated historic fitness data with the pre-existing fitness standard based, at least in part, on a result of the comparing; and generate an alert based on a detected deviation between the updated historic fitness data and the pre-existing fitness standard.

22. The apparatus of claim 21, wherein the particular user is identified by matching a biometric reading of the particular user against a database of users.

23. The apparatus of claim 21, wherein the particular user is identified by reading a Radio Frequency Identification (RFID) chip that comes into proximity with the exercise equipment.

24. The apparatus of claim 21, wherein the particular user is identified by communicating with a mobile communication device, associated with the particular user, using a short-range communication signal.

25. The apparatus of claim 21, wherein the particular user is identified based on a scanned bar code associated with the particular user.

26. The apparatus of claim 21, wherein the apparatus comprises a mobile communication device, and wherein the instructions comprise a software application that is installed on the mobile communication device.

27. The apparatus of claim 21, wherein the apparatus comprises a web-portal operatively connected to the exercise equipment through a network, and wherein the processing device is further configured to transmit the personalized fitness plan from the web-portal to a mobile communication device or a personal computer.

28. The apparatus of claim 21, wherein
the processing device is further configured to
initiate an emergency call to a medical response number in response to the alert.

29. The apparatus of claim 21, wherein the pre-existing fitness standard is based, at least in part, on the historic fitness data of the particular user.

30. The apparatus of claim 21, wherein the pre-existing fitness standard is associated with a population of similarly-aged individuals as the particular user.

31. An apparatus, comprising:
means for identifying a particular user;
means for receiving real-time vital data associated with the particular user;
means for retrieving historic fitness data associated with the particular user and updating the historic fitness data with the real-time vital data;
means for retrieving a pre-existing fitness standard comprising a combination of cardiovascular and aerobic data from individuals having a similar age as the particular user;
means for comparing the updated historic fitness data with the pre-existing fitness standard to generate a personalized fitness plan for re-aligning the updated historic fitness data with the pre-existing fitness standard based, at least in part, on a result of the comparing; and
means for transmitting the updated historic fitness data and the pre-existing fitness standard to a display on exercise equipment.

32. The apparatus of claim 31, wherein the means for identifying comprises a bar code scanner.

33. The apparatus of claim 31, wherein the means for identifying comprises a camera.

34. The apparatus of claim 31, wherein the means for identifying comprises an identification card reader.

35. The apparatus of claim 31, wherein the means for identifying comprises a Radio Frequency Identification (RFID) reader.

36. The apparatus of claim 31, wherein the means for receiving comprises means for measuring the real-time vital data while the particular user is operating the exercise equipment.

37. The apparatus of claim 36, wherein the real-time vital data comprises a heart rate of the particular user, and wherein the pre-existing fitness standard is based, at least in part, on a normalized heart rate associated with a particular mode of exercise using the exercise equipment.

38. The apparatus of claim 36, wherein the real-time vital data comprises a blood pressure of the particular user, and wherein the pre-existing fitness standard is based, at least in part, on a normalized blood pressure associated with using the exercise equipment.

39. The apparatus of claim 31, further comprising means for generating an alert when the real-time vital data indicates a deviation from the historic fitness data.

40. The apparatus of claim 31, wherein the personalized fitness plan comprises both an exercise program and a dietary program.

* * * * *